(12) United States Patent
Van Der Does et al.

(10) Patent No.: US 8,497,088 B2
(45) Date of Patent: Jul. 30, 2013

(54) PROCESS FOR THE PREPARATION OF BETA-LACTAM COMPOUNDS

(75) Inventors: Thomas Van Der Does, Wilnis (NL); Harold Monro Moody, Gulpen (NL); Theodorus Johannes Godfried Maria Van Dooren, Roermond (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 682 days.

(21) Appl. No.: 12/528,695

(22) PCT Filed: Mar. 10, 2008

(86) PCT No.: PCT/EP2008/052809
§ 371 (c)(1),
(2), (4) Date: Feb. 26, 2010

(87) PCT Pub. No.: WO2008/110527
PCT Pub. Date: Sep. 18, 2008

(65) Prior Publication Data
US 2011/0104748 A1    May 5, 2011

(30) Foreign Application Priority Data
Mar. 9, 2007   (EP) .................................. 07103850

(51) Int. Cl.
*C12P 1/00*   (2006.01)
(52) U.S. Cl.
USPC ................................ 435/41; 435/45; 435/177

(58) Field of Classification Search
USPC .................................................... 435/45, 177
See application file for complete search history.

(56) References Cited

U.S. PATENT DOCUMENTS
6,060,268 A    5/2000  De Vroom

FOREIGN PATENT DOCUMENTS
| EP | 0 544 205 | 6/1993 |
| WO | 92/01061 | 1/1992 |
| WO | 98/04732 | 2/1998 |
| WO | WO 2006003671 A1 * | 1/2006 |

OTHER PUBLICATIONS

Yang et al. "Enhanced enzymatic synthesis of a semi-synthetic cephalosprin, cefaclor, with in situ product removal", Biotechnology Letters, 2003, 25:1195-1198.*
InternatiOnal Search Report for PCT/EP2008/052809, mailed Jun. 24, 2008.

* cited by examiner

*Primary Examiner* — Bin Shen
(74) *Attorney, Agent, or Firm* — Nixon & Vanderhye P.C.

(57) ABSTRACT

The present invention describes a process for the synthesis of a semi-synthetic β-lactam compound from a nucleus and a side chain selected from the group consisting of D-phenylglycine and D-dihydro-phenylglycine in the form of a side chain ester and an enzyme catalyzing the coupling of the side chain ester to the nucleus characterized in that the side chain ester is not isolated as a solid intermediate.

9 Claims, 1 Drawing Sheet

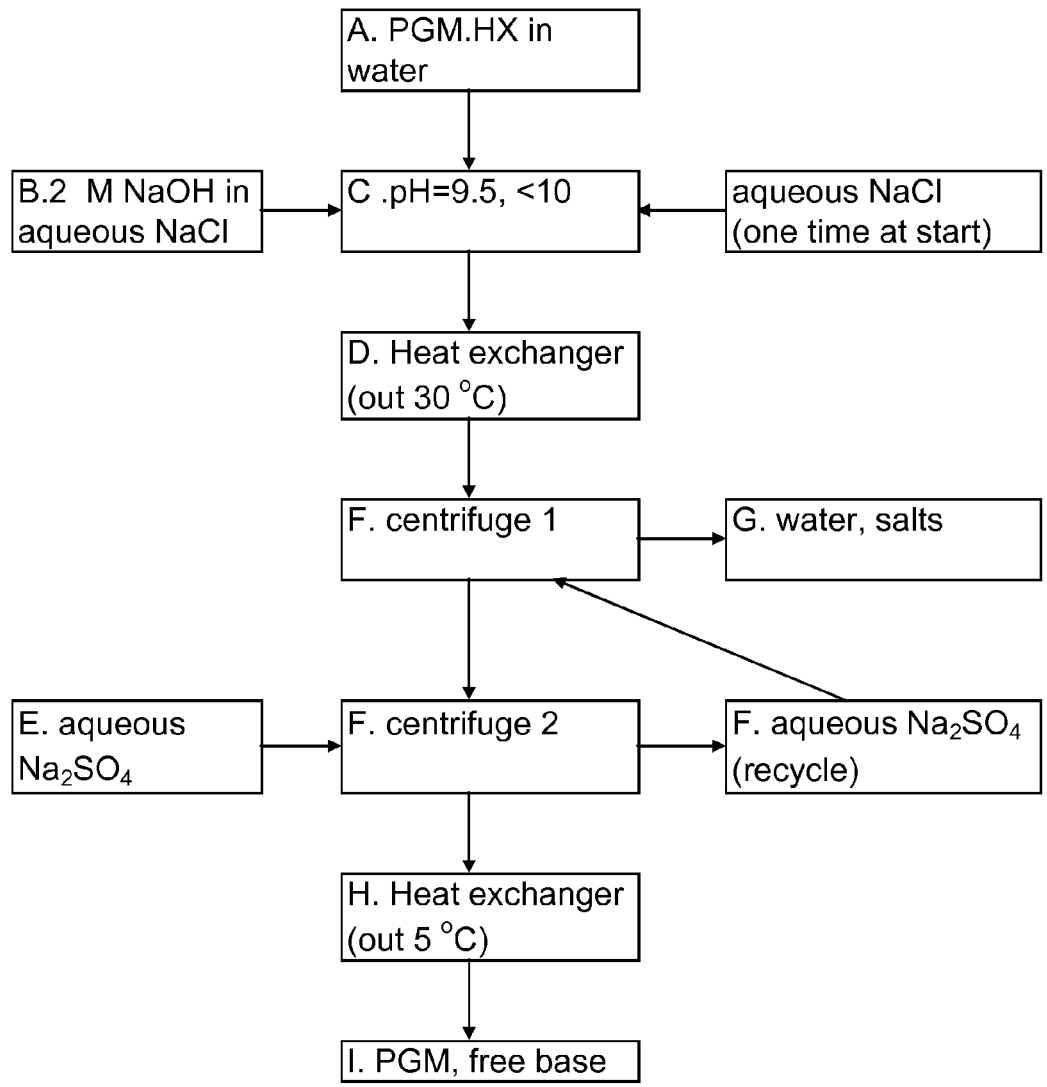

PROCESS FOR THE PREPARATION OF BETA-LACTAM COMPOUNDS

This application is the U.S. national phase of International Application No. PCT/EP2008/052809, filed 10 Mar. 2008, which designated the U.S. and claims priority to Europe Application No. 07103850.9, filed 9 Mar. 2007, the entire contents of each of which are hereby incorporated by reference.

The present invention relates to a process for the preparation of semi-synthetic β-lactam compounds by enzymatic acylation of the parent amino β-lactam with the acylating agent.

Enzymatic production of semisynthetic β-lactam antibiotics by acylation of the parent amino β-lactam moiety with a side chain acid derivative, such as an amide or an ester, has been widely described in the patent literature e.g. EP-A-339751, EP-A-473008, WO92/01061, WO93/12250, WO96/02663, WO96/05318, WO96/23796, WO97/04086, WO98/56946, WO99/20786, WO2005/00367, WO2006/069984, U.S. Pat. No. 3,816,253, and German patent documents 2163792 and 2621618. The enzymes used in the art are in most cases penicillin acylases obtained from *Escherichia coli* and are immobilized on various types of water-insoluble materials (e.g. WO97/04086).

A major disadvantage of the prior art processes is that the side chain esters must be isolated in a solid form in order to purify the side chain ester, for instance, to reduce the amount of free side chain in the ester. It has been found that, in particular in the case of the more hydrophobic side chains such as D-phenylglycine and D-dihydro-phenylglycine, the presence of free side chain in the subsequent enzymatic coupling reaction has a strong negative effect on the yield of the enzymatic coupling reaction. This is attributed to the fact that, due to the low solubility of the free side chains under the conditions of the enzymatic coupling reaction, there is an upper limit to the concentration of free side chain in the enzymatic coupling reaction. This limit is determined by the requirement that the free side chain should not crystallize or precipitate, because the precipitates negatively affect the processability of the enzymatic coupling reaction. Moreover, in the final steps of the downstream processing of the semi-synthetic β-lactam compound, the contaminating free side chain has to be removed, for instance with the mother liquor of a final crystallization step of the semi-synthetic β-lactam compound. At higher levels of free side chain, more mother liquor is required to remove the free side chain which in turn is responsible for higher losses of the semi-synthetic β-lactam compound. The unit operation which results in the isolation of the side chain ester in solid form complicates the production process of the semi-synthetic antibiotic and significantly contributes to the cost price thereof.

Therefore, there is an urgent need for a production process in which the side chain ester formed during the esterification reaction, can be used in the subsequent enzymatic coupling reaction without being isolated in a solid form.

WO98/04732 discloses in Examples 1, 3 and 4 the synthesis of cefprozil, cefadroxil and amoxicillin from 7-PACA, 7-ADCA and 6-APA respectively with the 2-hydroxyethyl-ester of D-4-hydroxy-phenylglycine whereby the ester after its synthesis is added directly to the subsequent enzymatic coupling reaction within being isolated in a solid form. D-4-hydroxy-phenylglycine has a very good solubility under the conditions of the enzymatic coupling reaction and therefore does not generate the problems during the enzymatic coupling reaction as are encountered for D-phenylglycine and D-dihydro-phenylglycine. In order to avoid their precipitation these may be present only at very low concentration as a result of their low solubility.

It is an object of the present invention to provide a production process for β-lactam derivatives of D-phenylglycine and D-dihydro-phenylglycine, such as Ampicillin, Cephalexin, Cefaclor and Cephradine, wherein the synthesis of the side chain ester is characterized by a high yield and the resulting side chain ester contains only low concentrations of free side chains and wherein the isolation of the side chain ester in a solid form in order to purify the side chain ester, is omitted.

"Nucleus" is defined herein as the β-lactam moiety of the semi-synthetic β-lactam and may be any penem or cephem, for instance 6-aminopenicillanic acid (6-APA), 7-aminodeacetoxy-cephalosporanic acid (7-ADCA), 7-aminocephalosporanic acid (7-ACA) or 7-amino-3-chloro-3-cephem-4-carboxylate (7-ACCA).

"Side chain" is defined herein as the moiety which in the semi-synthetic β-lactam compound is attached to the 6-amino or 7-amino position in the nucleus as defined herein, for instance D-phenylglycine in Ampicillin, Cephalexin, Cefaclor or D-dihydro-phenylglycine in Cephradine.

"Free side chain" is the underivatised form of the side chain, for instance D-phenylglycine or D-dihydro-phenylglycine.

"Side chain ester" is the ester form of the free side chain whereby the carboxyl group of the free side chain is esterified to an alcohol, for instance D-phenylglycine methyl ester or D-dihydro-phenylglycine methyl ester. The side chain ester may be in the form of the free base or as a salt, for instance as the HCl-salt and the side chain ester may be in a solid form or dissolved in a suitable solvent.

"Ratio" is defined herein as:

$$\frac{[\text{Amount of side chain ester}]}{[\text{Amount of side chain ester}] + [\text{Amount of free side chain}]}$$

whereby the amounts are expressed in moles

In one aspect, the invention provides a process for the synthesis of a semi-synthetic β-lactam compound from a nucleus and a side chain selected from the group consisting of D-phenylglycine and D-dihydro-phenylglycine in the form of a side chain ester and an enzyme catalyzing the coupling of the side chain ester to the nucleus characterized in that the side chain ester is not isolated as a solid intermediate. The process may for instance comprise the following steps:

a) converting a free side chain selected from the group consisting of D-phenylglycine and D-dihydro-phenylglycine with an alcohol to form a mixture comprising the corresponding side chain ester; the formation of the side chain ester in this step preferably results in a mixture with a conversion which is expressed by the "ratio" as defined hereinbefore and whereby the ratio is preferably ≧85%, more preferably ≧90%, more preferably ≧95, more preferably ≧96, more preferably ≧97, more preferably ≧98%, most preferably ≧99%;

b) forming the semi-synthetic β-lactam compound by mixing the mixture obtained in step a) with a nucleus and the enzyme to form the semi-synthetic β-lactam compound, with the proviso that the side chain ester formed in step (a) is not isolated as a solid intermediate.

The nucleus used in the process of the present invention and as defined herein before, may be selected from the group consisting of 6-aminopenicillanic acid (6-APA), 7-aminodeacetoxy-cephalo-sporanic acid (7-ADCA), 7-aminocephalosporanic acid (7-ACA) and 7-amino-3-chloro-3-cephem-4-carboxylate (7-ACCA) so as to give semisynthetic penicillins (derivatives of 6-APA) and semisynthetic cephalosporins (derivatives of 7-ADCA, 7-ACA and 7-ACCA) respectively. A preferred embodiment of the present invention is the process for the preparation of a semi-synthetic β-lactam compound selected from the group consisting of ampicillin, cephalexin, cephradine, cefaclor.

In the conversion step (step (a)) of the process of the invention a free side chain selected from the group consisting of D-phenylglycine and D-dihydro-phenylglycine is converted with an alcohol to form a mixture comprising the corresponding side chain ester. The alcohol used in the process of the invention may be selected from the group consisting of methanol and ethanol thereby forming the methyl ester and ethyl ester of the side chain respectively. The most preferred alcohol is methanol. Step (a) may be carried out in several ways.

One embodiment of conversion step (a) comprises heating of a mixture comprising a free side chain selected from the group consisting of D-phenylglycine and D-dihydro-phenylglycine, an alcohol selected on the basis of the desired ester to be formed, for example methanol to obtain the methyl ester or ethanol to obtain the ethyl ester, and a strong acid such as sulfuric acid, under reflux at a temperature between 20 and 120° C., more preferably between 40 and 100° C. When using methanol as the alcohol, the temperature is preferably between 60 and 80° C. When using ethanol as the alcohol, the temperature is preferably between 65 and 100° C. Suitable conditions may be found in the comparative examples 1 and 2 as disclosed in EP-A-0544205.

Another embodiment of conversion step (a) comprises an improvement of the previous embodiment and comprises addition of the alcohol as a liquid or a gas to the reaction mixture while distilling off the alcohol and the water from the reaction (e.g. as described in EP-A-0544205).

A highly preferred embodiment of conversion step (a) and which results in a mixture comprising the methyl ester of the side chain comprises the following steps:
1. refluxing a reaction mixture comprising a free side chain selected from the group consisting of D-phenylglycine and D-dihydro-phenylglycine, methanol and a strong acid such as sulfuric acid for a certain time, for example between 0.5 and 5 hours, preferably between 1 hour and 3 hours, more preferably between the 1.5 and 2.5 hours at a temperature in the temperature between 20 and 120° C., more preferably between 20 and 100° C., more preferably between 40 and 100° C., most preferably between 60 and 80° C.; followed by
2. concentrating the mixture at a temperature between 40 and 100° C., preferably between 60 and 90° C., more preferably between 70 and 80° C. The pressure during this step may initially be atmospheric and may during the concentrating step be reduced to preferably 50 mbar or less, more preferably to 40 mbar or less, more preferably to 30 mbar or less and most preferably to 20 mbar or less. The concentrating step is continued until more than 30% of the water present before the concentrating step is removed, preferably more than 40% of the water is removed, preferably more than 50% of the water is removed, preferably more than 70% of the water is removed, preferably more than 80% of the water is removed and most preferably more than 90% of the water is removed.
3. adding methanol, preferably an amount so as to obtain the initial volume of the reaction mixture before the concentrating step or an amount which is less than the initial volume of the reaction mixture, e.g. $\leqq 90$ or $\leqq 80$ or $\leqq 70$ or $\leqq 60$ or $\leqq 50$ or $\leqq 40$ or $\leqq 30$ or $\leqq 20\%$ of the initial volume of the reaction mixture. The amount of methanol added may also be more than the initial volume of the reaction mixture.
4. optionally repeating steps 1-3 one or more times, preferably at least once, preferably 2 times, more preferably 3 times, more preferably 4 times, more preferably 5 times, more preferably 6 times, more preferably 7 times, more preferably 8 times, more preferably 9 times, more preferably 10 times. It was found that by repeating these steps the "ratio" as defined hereinbefore of the formation of methyl ester increased significantly. For instance, after carrying out steps (a)-(c) only once, a "ratio" between 75-85% may be obtained, after repeating steps (a)-(c) once, a "ratio" between 85-95% may be obtained, and after repeating steps (a)-(c) 2 times, a "ratio" between 95-97% may be obtained, and after repeating steps (a)-(c) 3 times, a "ratio" between 97-98% may be obtained and after repeating steps (a)-(c) 4 times, a "ratio" between 98-99% may be obtained and after repeating steps (a)-(c) 5 times, a "ratio" between 99-99.5% may be obtained and after repeating steps (a)-(c) more than 5 times a "ratio of more than 99.5% may be obtained.

Another highly preferred embodiment of conversion step (a) and which results in a mixture comprising the ethyl ester of the side chain comprises the following steps:
1. refluxing a reaction mixture comprising a free side chain selected from the group consisting of D-phenylglycine and D-dihydro-phenylglycine, ethanol and a strong acid such as sulfuric acid for a certain time, for example between 0.5 and 5 hours, preferably between 1 hour and 3 hours, more preferably between the 1.5 and 2.5 hours at a temperature in the temperature between 20 and 120° C., more preferably between 20 and 100° C., more preferably between 40 and 100° C., most preferably between 65 and 100° C.; followed by
2. concentrating the mixture at a temperature between 40 and 100° C., preferably between 60 and 90° C., more preferably between 70 and 80° C. The pressure during this step may initially be atmospheric and may during the concentrating step be reduced to preferably 50 mbar or less, more preferably to 40 mbar or less, more preferably to 30 mbar or less and most preferably to 20 mbar or less. The concentrating step is continued until more than 30% of the water present before the concentrating step is removed, preferably more than 40% of the water is removed, preferably more than 50% of the water is removed, preferably more than 70% of the water is removed, preferably more than 80% of the water is removed and most preferably more than 90% of the water is removed.
3. adding ethanol, preferably an amount so as to obtain the initial volume of the reaction mixture before the concentrating step or an amount which is less than the initial volume of the reaction mixture, e.g. $\leqq 90$ or $\leqq 80$ or $\leqq 70$ or $\leqq 60$ or $\leqq 50$ or $\leqq 40$ or $\leqq 30$ or $\leqq 20\%$ of the initial volume of the reaction mixture. The amount of ethanol added may also be more than the initial volume of the reaction mixture.
4. optionally repeating steps 1-3 one or more times, preferably at least once, preferably 2 times, more preferably 3 times, more preferably 4 times, more preferably 5 times, more preferably 6 times, more preferably 7 times, more preferably 8 times, more preferably 9 times, more preferably 10 times. It was found that by repeating these steps the "ratio" as defined hereinbefore of the formation of ethyl ester increased significantly. For instance, after carrying out steps (a)-(c) only once, a "ratio" between 75-85% may be obtained, after repeating steps (a)-(c) once, a "ratio"

between 85-95% may be obtained, and after repeating steps (a)-(c) 2 times, a "ratio" between 95-97% may be obtained, and after repeating steps (a)-(c) 3 times, a "ratio" between 97-98% may be obtained and after repeating steps (a)-(c) 4 times, a "ratio" between 98-99% may be obtained and after repeating steps (a)-(c) 5 times, a "ratio" between 99-99.5% may be obtained and after repeating steps (a)-(c) more than 5 times a "ratio of more than 99.5% may be obtained.

In all embodiments of step (a), preferably the following molar ratio of alcohol versus free side chain is used: between 3 and 25, more preferably between 5 and 25 and most preferably between 6 and 10. Also, in all embodiments of step (a), preferably the following molar ratio of strong acid (in equivalents, e.g. one mole of hydrochloric acid is one equivalent and one mole of sulfuric acid is two equivalents) versus free side chain is used: between 0.9 and 10, more preferably between 1 and 5 and most preferably between 2 and 3. The skilled person will be able to optimize the reaction conditions depending on the side chain and the alcohol selected without undue experimentation.

Before forming the semi-synthetic β-lactam compound in step (b), the mixture obtained in step (a) may be purified so as to obtain a mixture with a high "ratio" as defined hereinbefore. The ratio of the mixture which is to be used in step (b) of the process of the invention is preferably ≧85, more preferably ≧90, more preferably ≧95, more preferably ≧96, more preferably ≧97, more preferably ≧98, most preferably ≧99%.

One embodiment of the purification step involves the precipitation and removal of the free side chain from the side chain ester. This may be achieved by adjusting the pH of the mixture obtained in step (a) to a value between 2 and 6.5, preferably between 2.5 and 5, most preferred between 3 and 4 by adding a suitable base, such as NaOH, ammonia, KOH. In another embodiment, the reaction mixture obtained in step (a) may be added to a suitable amount of water or to an alcohol or to a mixture of water and alcohol, followed by adjusting the pH to a value between 2 and 6.5, preferably between 2.5 and 5, most preferred between 3 and 4 by adding a suitable base, such as NaOH, ammonia, KOH. After adjusting the pH to the desired value, the pH may be maintained at the desired value by adding the suitable base. Under these conditions, a precipitate comprising the free side chain may be formed. After a suitable time, the precipitate may be filtered off using known techniques. The filtrate comprises the side chain ester. In order to be used directly in step (b) of the process of the invention, the pH of the filtrate is brought to a pH between 1 and 6, preferably between 1 and 4, most preferably between 1.5 and 3, after which the alcohol is removed by evaporation using known techniques.

Another embodiment of the purification step involves the formation of a two or multi-phase system comprising an organic phase containing the side chain ester derivative and a minor amount of free side chain and an aqueous phase containing the free side chain and, optionally, salt. This may be achieved by adjusting the pH of the mixture obtained in step (a) at a value between 7.5 and 10, preferably between 8.5 and 9.5, most preferred between 8.8 and 9.2 by adding a suitable base, such as NaOH, ammonia, KOH. In another embodiment, the reaction mixture obtained in step (a) may be added to a suitable amount of water, an alcohol or to a mixture of water and alcohol, followed by adjusting the pH at a value between 7.5 and 10, preferably between 8.5 and 9.5, most preferred between 8.8 and 9.2 by adding a suitable base, such as NaOH, ammonia, KOH. After adjusting the pH to the desired value, the pH may be maintained at the desired value by adding the suitable base. Optionally, the water may be in the form of an aqueous salt (e.g. NaCl) solution. The free side chain may also form a precipitate. The various phases in the multi-phase system may be separated using known techniques. Optionally the organic phase may be washed with water or an aqueous salt solution. The water phase of the wash may be recycled to a suitable process stream in order to avoid loss of yield. This process stream may be the reaction mixture as obtained after step (a) or the after the pH adjustment as described.

A highly preferred embodiment of purification step combines the two previous embodiments, i.e. first adjusting the pH of the mixture obtained in step (a) between 2 and 6.5, preferably between 2.5 and 5, most preferred between 3 and 4 and filtering off the precipitate formed and subsequently adjusting the pH of the filtrate obtained at a pH between 7.5 and 10, preferably between 8.5 and 9.5, most preferred between 8.8 and 9.2 and separating the various phases in the multi-phase system obtained using known techniques.

It has been surprisingly found that in the previous two embodiments wherein the multi-phase system is formed at a pH between 7.5 and 10, preferably between 8.5 and 9.5, most preferred between 8.8 and 9.2, may yield an ester, preferably selected from the group consisting of D-phenylglycine-methylester, D-phenylglycine-ethylester, D-dihydro-phenylglycine-methylester and D-dihydro-phenylglycine-ethylester, in the free base form, whereby the ester has the following properties:

an e.e. (enantiomeric excess) preferably equal to or greater than 90%, more preferably equal to or greater than 95%, preferably equal to or greater than 96%, preferably equal to or greater than 97%, preferably equal to or greater than 98% and most preferably equal to or greater than 99%; and a salt content preferably of 20 mole % or less, more preferably of 10 mole % or less, more preferably of 5 mole % or less, more preferably of 2 mole % or less, most preferably of 1 mole % or less, expressed as moles of salt relative to moles of ester.

a "ratio" as defined hereinbefore of preferably ≧85, more preferably ≧90, more preferably ≧95, more preferably ≧96, more preferably ≧97, more preferably ≧98%, most preferably ≧99%.

In step (b) of the process of the invention, the semi-synthetic β-lactam compound is formed by mixing the mixture obtained in step (a), optionally purified as described hereinbefore with a nucleus and a suitable enzyme, preferably an immobilized enzyme, to form the corresponding semi-synthetic β-lactam compound, with the proviso that the side chain ester formed in step (a) and optionally purified is not isolated as a solid intermediate. Step (b) may be carried according to any of the processes known in the art and which have been cited hereinbefore. For instance, the synthesis of ampicillin may be carried out as described in EP-A-339751 or WO98/56946. Likewise, the synthesis of cephalexin may be carried out as described in WO96/23796. The synthesis of cephradine may be carried as has described in WO2005/003367 and the synthesis of cefaclor may be carried out as has been described in WO2006/069984.

After the enzymatic coupling, the semi-synthetic beta-lactam antibiotic can be recovered using known methods. For instance, the enzyme reactor may be discharged through the bottom sieve using upwards stirring. The resulting semi-synthetic beta-lactam antibiotic suspension may then be filtered through a glass filter.

Due to the low amount of free side chain present after the enzymatic coupling reaction, crystallization of the final semisynthetic beta-lactam antibiotic may be carried out at high concentrations of the beta-lactam antibiotic which results in high yields.

In a second aspect, the invention provides an ester, preferably selected from the group consisting of D-phenylglycine-methylester, D-phenylglycine-ethylester, D-dihydro-phenylglycine-methylester and D-dihydro-phenylglycine-ethylester, in the free base form, whereby the ester has the following properties:

an e.e. (enantiomeric excess) preferably equal to or greater than 90%, more preferably equal to or greater than 95%, preferably equal to or greater than 96%, preferably equal to or greater than 97%, preferably equal to or greater than 98% and most preferably equal to or greater than 99%; and a salt content preferably of 20 mole % or less, more preferably of 10 mole % or less, more preferably of 5 mole % or less, more preferably of 2 mole % or less, most preferably of 1 mole % or less, expressed as moles of salt relative to moles of ester.

a "ratio" as defined hereinbefore of preferably ≧85, more preferably ≧90, more preferably ≧95, more preferably ≧96, more preferably ≧97, more preferably ≧98%, most preferably ≧99%.

It will be evident for the skilled person that an ester in the free base form is provided having any value of the e.e. listed in combination with any value of the salt content listed and in combination with any value of any of the "ratio"

In a third aspect, the invention provides a process for the production of the ester in the free base form of the invention with the properties as defined above. The process may comprise mixing a salt of the side chain ester with a base in an aqueous environment thereby producing a two phase system and separating the side chain ester in free base form from the aqueous phase.

The salt of the side chain ester may be any suitable salt such as the HCl-salt. The salt may be in a solid form or may be in a liquid from, i.e. a solution in water or another suitable solvent, optionally containing other components such as salts. The base which is mixed with the salt of the side chain ester may be any base, preferably a strong base such as sodium hydroxide, potassium hydroxide or ammonia.

In the two phase system formed, the organic phase with the side chain ester in the free base form contains preferably no or only very low levels of free side chain, i.e. the "ratio" as defined hereinbefore preferably being ≧85, more preferably ≧90, more preferably ≧95, more preferably ≧96, more preferably ≧97, more preferably ≧98, most preferably ≧99, while the aqueous phase containing the free side chain and optionally salts contains preferably no or only very low levels of side chain ester.

The two phase system may be formed as described hereinbefore under the purification steps in which the multi-phase system is formed at a pH between 7.5 and 10, preferably between 8.5 and 9.5, most preferred between 8.8 and 9.2

The various phases in the multi-phase system may be separated using known techniques. Suitable methods are those that make use of the density difference between the various phases. Depending on the scale, separation may be obtained using normal gravity, or, preferably using centrifugal forces, either in batch mode, or more preferably in continuous mode. A preferred continuous centrifugation process is described in detail in FIG. 1 and Example 5 for PGM. This process may be applied to any ester, preferably selected from the group consisting of D-phenylglycine-methylester, D-phenylglycine-ethylester, D-dihydro-phenylglycine-methylester and D-dihydro-phenylglycine-ethylester, in the free base form.

FIG. 1

A. A container containing a PGM solution, obtainable as described in example 4.

B. A container containing a solution of NaOH (65 g/kg solution) and NaCl (211 g/kg solution) in water (724 g/kg solution). The contents of the container is kept between 3 and 5° C.

C. A 10 l glass vessel equipped with agitator, baffles, thermometer, pH meter, an inlet for the PGM solution, an inlet NaOH/NaCl solution and an outlet for the reaction mixture. The vessel is placed in a cooling bath.

D. A heat exchanger (internal volume 1 l) to raise the temperature of the reaction mixture to 30° C. before introduction in the centrifuges.

E. A container containing a 25% (w/w) solution of $Na_2SO_4$. The contents of the container were warmed to 30° C.

F. Two Robatel BXP130 extraction centrifuges (liquid/liquid extractors, diameter of bowl 125 mm, volume of bowl 1.4 l, diameter light phase weir 61 mm, diameter heavy phase weir 66 mm). The inlets and outlets of the centrifuges were connected as follows:

reaction mixture from the 10 l vessel was introduced in the light phase inlet of centrifuge 1

25% (w/w) solution of $Na_2SO_4$ was introduced in the heavy phase inlet of centrifuge 2 heavy outlet of centrifuge 1 was connected to the receiving container (G). After the experiment the contents were discarded.

light phase outlet of centrifuge 1 was connected to the light phase inlet of centrifuge 2 heavy phase outlet of centrifuge 2 was connected to the heavy phase inlet of centrifuge 1 light phase outlet of centrifuge 2 was, by means of a peristaltic pump, pumped through a heat exchanger to cool this process stream to 3-5° C.

G. A receiving container to collect aqueous phase from centrifuge 1

H. A heat exchanger to cool the process stream to 3-5° C.

I. A vessel, kept cool at 3-5° C. to collect PGM, free base

Not shown in FIG. 1 are the following peristaltic pumps:

A peristaltic pump to pump the PGM solution to the 10 l vessel

A peristaltic pump to pump the NaOH/NaCl solution to the 10 l vessel. The flow of this pump was controlled by the pH meter.

A peristaltic pump to pump the reaction mixture via a heat exchanger to the centrifuges.

A peristaltic pump to pump 25% (w/w) solution of Na2SO4 to the centrifuges.

EXAMPLES

Example 1 a) Synthesis of a Phenylglycine-Methylester (PGM) Solution 90 g D-phenylglycine was suspended in 170 ml methanol and 73.2 g concentrated sulfuric acid was added. The mixture was kept at reflux for 2 hours at approximately 73° C. and concentrated at a reduced pressure using a vacuum pump. The pressure dropped from atmospheric to 20 mBar while at the same time the temperature of the reaction mixture increased from 40 to 80° C.

170 ml methanol was added and the mixture was kept again at reflux for 2 hours and concentrated at reduced pressure. Again, 170 ml methanol was added and the mixture was kept at reflux for 2 hours and concentrated at reduced pressure.

Finally, 125 ml methanol was added. At this stage, the "ratio" as defined hereinbefore was 95%.

The solution was dosed into a second reactor, which had been pre-charged with 20 ml methanol, in 1 hour at 20° C. The pH was kept at 3.5 with ammonia. A solid was formed, which was removed by filtration. The resulting mother liquor was diluted with 25 ml water and concentrated at reduced pressure (p=20 mm Hg, T=40-45° C.). Finally 207.5 g D-phenylglycine-methylester (PGM) solution was obtained. The "ratio" of the resulting solution was 99%.

b) Enzymatic Synthesis of Cephalexin

A reactor with a 175 μm sieve bottom was filled with 15 g immobilized *Escherichia coli* PenG acylase mutant Phe-B24-Ala. Subsequently 21.4 g 7-ADCA and 95 g water were added at 25° C. and the pH was adjusted to 7.0 with 25% ammonia.

38 g PGM solution as obtained in step a) (above) was dosed into the reactor at a constant rate in 120 min. The pH was maintained at 7.0 with ammonia. The temperature was kept at 25° C. After 30 min, 0.25 g solid cephalexin (seed) was added. Crystallization of cephalexin started at 45 min. From 120 to 150 min, the pH was kept at 7.0 with 25% sulfuric acid. Subsequently, the pH was decreased to 5.7 with 25% sulfuric acid.

c) Recovery of Cephalexin

The reactor was discharged through the bottom sieve with upwards stirring. The resulting cephalexin suspension was filtered through a glass filter. The resulting mother liquor was transferred back into the reactor. This sequence of steps was repeated five times. Subsequently, the enzyme was washed with 2×10 ml water. In this way, 98% of cephalexin was separated from the solid biocatalyst.

The cephalexin wet cake, mother liquor and wash water were combined, and the temperature was maintained at 2° C. The pH of the combined wet cake and mother liquors was decreased to 1.5 with concentrated sulfuric acid and the resulting solution was filtered through a 0.45 μm filter.

A crystallization reactor was filled with 20 g water and 1.0 g of cephalexin (seed). The above-mentioned acidic cephalexin solution was dosed into the crystallization reactor in 80 minutes at 30° C. The pH was kept at 5.0 with ammonia. Subsequently, the suspension was stirred at 20° C. for another 30 min. The suspension was filtered through a glass filter and the wet cake was washed with 2×15 ml water and 2×15 ml acetone. After drying, 32.6 g cephalexin monohydrate was obtained (purity ≧99.8%).

Example 2 a) Synthesis of D-Dihydrophenylglycine-Methylester (DH-PGM) Solution 90 g D-dihydro-phenylglycine (DHPG) was suspended in 200 ml methanol and 73.2 g concentrated sulfuric acid was added. The mixture was kept at reflux for 2 hours at approximately 73° C. and concentrated at a reduced pressure using a vacuum pump. The pressure dropped from atmospheric to 20 mBar while at the same time the temperature of the reaction mixture increased from 40 to 80° C.

170 ml methanol was added and the mixture was kept again at reflux for 2 hours and concentrated at reduced pressure. Again, 170 ml methanol was added and the mixture was kept at reflux for 2 hours and concentrated at reduced pressure. Finally, 125 ml methanol was added. At this stage, the "ratio" as defined herein before was 94.8%.

The solution was dosed into a second reactor, which had been pre-charged with 20 ml methanol, in 1 hour at 20° C. The pH was kept at 3.5 with ammonia. A solid was formed, which was removed by filtration. The resulting mother liquor was diluted with 25 ml water, decolorized with 3 g charcoal (activated carbon) and concentrated at reduced pressure (p=20 mm Hg, T=40-45° C.). Finally 217.6 g DHPGM solution was obtained. The "ratio" of the resulting solution was 99.2%.

b) Enzymatic Synthesis of Cephradine

This step was carried out as described in WO2005/003367.

Example 3 a) Synthesis of a D-Phenylglycine-Methylester (PGM) Solution 90 g D-phenylglycine was suspended in 170 ml methanol and 73.2 g concentrated sulfuric acid was added. The mixture was kept at reflux for 2 hours at approximately 73° C. and concentrated at a reduced pressure using a vacuum pump. The pressure dropped from atmospheric to 20 mBar while at the same time the temperature of the reaction mixture increased from 40 to 80° C.

170 ml methanol was added and the mixture was kept again at reflux for 2 hours and concentrated at reduced pressure. Again, 170 ml methanol was added and the mixture was kept at reflux for 2 hours and concentrated at reduced pressure. Finally, 125 ml methanol was added. This mixture is called esterification mixture.

Most of the esterification mixture (about 95%) was dosed into a second reactor, which had been pre-charged with 40 ml water, in 1 hour at 25-30° C. The pH was kept at 3.5 with 8 M NaOH (consumption 34 g). A solid was formed, which was removed by filtration. The resulting mother liquor was mixed with esterification mixture (about 5%) to reduce the pH of the filtrate to pH=2. The mixture was concentrated at reduced pressure (p=20 mm Hg, T=40-45° C.). Finally 190 g of a viscous mixture was obtained.

b) Preparation of 2 M NaOH in 5 M NaCl 80 g NaOH was dissolved in 149 ml water. The solution was diluted to 1000 ml by addition of 5 M NaCl. About 840 ml of 5 M NaCl is required to adjust the volume to 1000 ml.

c) Synthesis of PGM as a Free Base

Viscous mixture as obtained in a) was mixed with 120 ml of 5 M NaCl at 40° C. This mixture was added in the course of 20 minutes to 50 ml of 5 M NaCl while pH was maintained at pH=9 by addition of 2 M NaOH in 5 M NaCl. Temperature of the mixture was maintained at 20° C. The mixture was transferred to a separation funnel, and the mixture was left to settle for 20 minutes. Subsequently the layers were separated. The upper layer was mixed with 120 ml of 5 M NaCl at room temperature. The mixture was transferred to a separation funnel, and left to settle for 20 minutes. The layers were separated. The upper layer was centrifuged at 5000 rpm. A minor bottom layer was formed, which was removed from the oily product. 95 g of PGM, free base was obtained. Assay: 85%; e.e. =97%; Yield based on PG input in step (a): 82%. Assay of PG in PGM, free base: 0.2% (i.e. a "ratio" of 99.8%).

d) Synthesis of Ampicillin

This step was carried out as described in WO98/56946 for the synthesis of ampicillin from 6-APA and the PGA, i.e. the amide derivative of PG instead of the methylester.

Example 4

Synthesis of a D-Phenylglycine-Methylester (PGM) Solution 135 g D-phenylglycine was suspended in 252 ml methanol and 107 g concentrated sulfuric acid (98%) was added. The mixture was kept at reflux for 2 hours at approximately 73° C. and concentrated at a reduced pressure using a vacuum pump. The pressure dropped from atmospheric to 20 mBar while at the same time the temperature of the reaction mixture increased from 40 to 80° C. 126 ml (100 g) methanol was added, the mixture was kept at reflux for 1 hour at approximately 81° C. and concentrated as described before.

The procedure was repeated for another four times (addition of methanol, reflux and concentrating). Finally, 126 ml methanol was added; the solution was refluxed for another hour and cooled to ambient temperature.

15 ml ammonia was dosed with constant rate in 35 min up to pH 2.3-2.4. 75 ml water was added. Methanol was distilled off at reduced pressure and a temperature below 50° C. The pH of the final PGM solution was 2.0 and the "ratio" was 99.0%.

Example 5

Production of PGM Free Base by Use of Counter Current Extraction Centrifuges

The process line as depicted in FIG. 1 was operated as follows:
- Centrifuges were started and operated at 2400 rpm
- 25% (w/w) solution of $Na_2SO_4$ was introduced in centrifuge 2 with a flow rate of 7.5 kg/h. The reaction mixture (see below) was introduced in centrifuge 1 after there was flow from the heavy phase outlet of centrifuge 1
- 1000 ml 5.3 M NaCl was added to the 10 l vessel
- The contents of the 10 l vessel was cooled to 8-10° C.
- The PGM solution was introduced to 10 l vessel with a flow of 15 kg/h
- The pH in the 10 l vessel was maintained at pH=9.7 by addition of NaOH/NaCl solution
- The volume in the 10 l vessel was maintained at 5 l by adjustment of the flow of reaction mixture out of the vessel
- The temperature in the 10 l vessel was maintained at 8-10° C.
- The reaction mixture of the 10 l vessel was pumped through a heat exchanger and thereby warmed up to 30° C. Subsequently the reaction mixture was introduced in centrifuge 1
- Light phase from centrifuge 2 was cooled via a heat exchanger to 3-5° C. and stored in vessel at 3-5° C.
- Light phase was applied in conversion to ampicillin in less than 4 h after production of light phase.

The invention claimed is:

1. A process for the synthesis of a semi-synthetic β-lactam compound from a nucleus and a side chain selected from the group consisting of D-phenylglycine and D-dihydro-phenylglycine in the form of a side chain ester and an enzyme catalyzing the coupling of the side chain ester to the nucleus comprising the steps of
    (a) converting a free side chain selected from the group consisting of D-phenylglycine and D-dihydro-phenylglycine with an alcohol to form a mixture comprising the corresponding side chain ester;
    (b) forming the semi-synthetic β-lactam compound by mixing the mixture obtained in step (a) with a nucleus and the enzyme to form the semi-synthetic β-lactam compound,
    with the proviso that the side chain ester formed in step (a) is not isolated as a solid intermediate.

2. Process according to claim 1 wherein the mixture obtained in step (a) is purified before forming the semi-synthetic β-lactam compound in step (b).

3. Process according to claim 1 wherein the nucleus is selected from the group consisting of 6-aminopenicillanic acid (6-APA), 7-amino-deacetoxy-cephalosporanic acid (7-ADCA), 7-aminocephalosporanic acid (7-ACA) and 7-amino-3-chloro-3-cephem-4-carboxylate (7-ACCA).

4. Process according to claim 1 wherein the semi-synthetic β-lactam compound is selected from the group consisting of Ampicillin, Cephalexin, Cephradine and Cefaclor.

5. Process according to claim 1 wherein the alcohol is methanol or ethanol.

6. Process according to claim 5 wherein the alcohol is methanol.

7. Process according to claim 1 wherein the enzyme is a penicillin G acylase.

8. Process according to claim 7 wherein the penicillin G acylase is from *Escherichia coli*.

9. Process according to claim 7 wherein the enzyme is in an immobilized form.

* * * * *